United States Patent [19]

Cianci et al.

[11] Patent Number: 4,501,584

[45] Date of Patent: Feb. 26, 1985

[54] LIQUID DRAINAGE SYSTEM WITH FORMED HINGED SUPPORT SHEET

[75] Inventors: James P. Cianci, Cary; William J. Dunn, Libertyville, both of Ill.

[73] Assignee: The Kendall Company, Boston, Mass.

[21] Appl. No.: 472,402

[22] Filed: Mar. 4, 1983

[51] Int. Cl.[3] .............................................. A61M 1/00

[52] U.S. Cl. ....................................... 604/322; 383/6; 248/95

[58] Field of Search ....................... 383/6, 7, 9, 12, 13, 383/22, 24; 604/322-326; 128/767, DIG. 24; 248/95, 99, 312, 318, 322

[56] References Cited

U.S. PATENT DOCUMENTS

| | | | |
|---|---|---|---|
| 3,254,817 | 6/1966 | Bartz | 248/95 |
| 3,534,738 | 10/1970 | Huck | 248/95 |
| 4,305,405 | 12/1981 | Meisch | 128/767 |
| 4,312,352 | 1/1982 | Meisch et al. | 128/275 |

*Primary Examiner*—C. Fred Rosenbaum
*Assistant Examiner*—J. L. Kruter
*Attorney, Agent, or Firm*—Powell L. Sprunger

[57] ABSTRACT

A liquid drainage system comprising, a receptacle having a chamber to receive the liquid, and a drainage tube communicating with the chamber. The system has a formed sheet of flexible material, with the sheet being of one-piece construction. The sheet has an elongated bar received in an upper portion of the receptacle, a first connecting portion extending from one side of the bar at a generally central location thereof, a first hinge extending across the sheet at an outer end of the first connecting portion, and a second elongated connecting portion extending from the first hinge on a side of the first hinge opposite the first connecting portion. The second connecting portion is flexed about the first hinge to align the first and second connecting portions in a facing relationship. The sheet has second and third hinges extending along opposed sides of the second connecting portion, and first and second hook members connected to the second and third hinges. The hook members have downwardly extending outer ends. The hook members are movable between a first position generally perpendicular to the receptacle to support the receptacle from an object, and a second position generally aligned with the receptacle with the outer ends of the hook members being located in front of the bar to form a handle to carry the receptacle.

4 Claims, 4 Drawing Figures

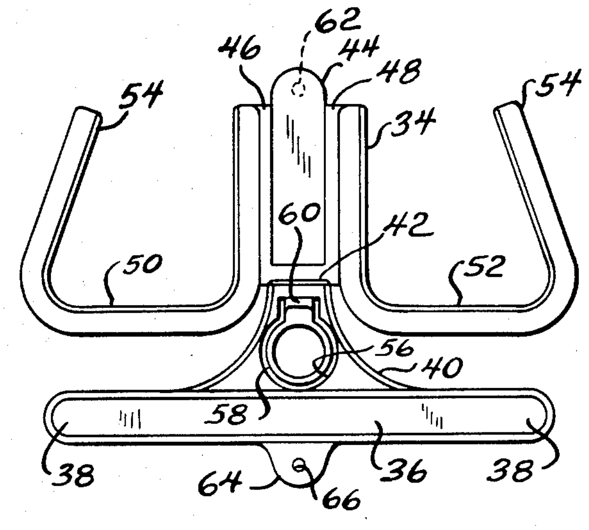
FIG. 1
FIG. 2
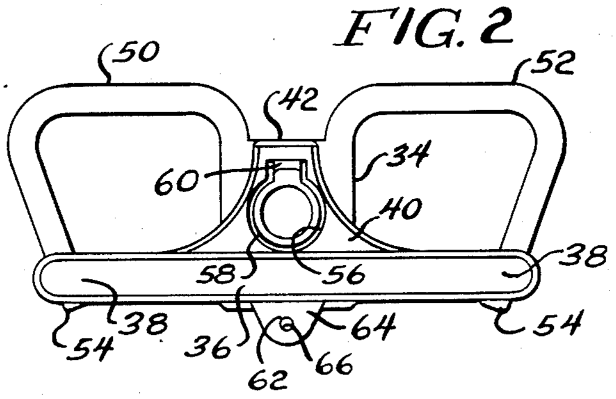
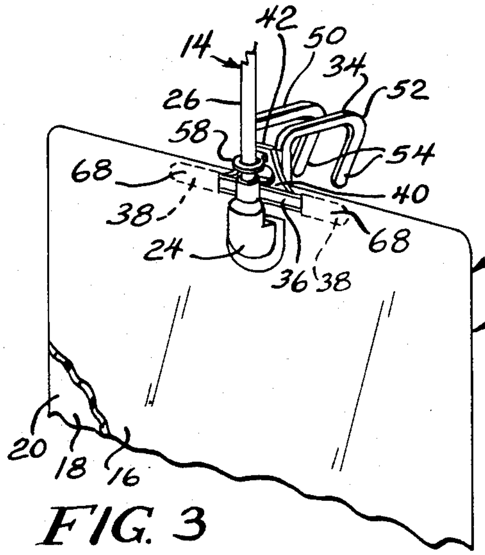
FIG. 3
FIG. 4
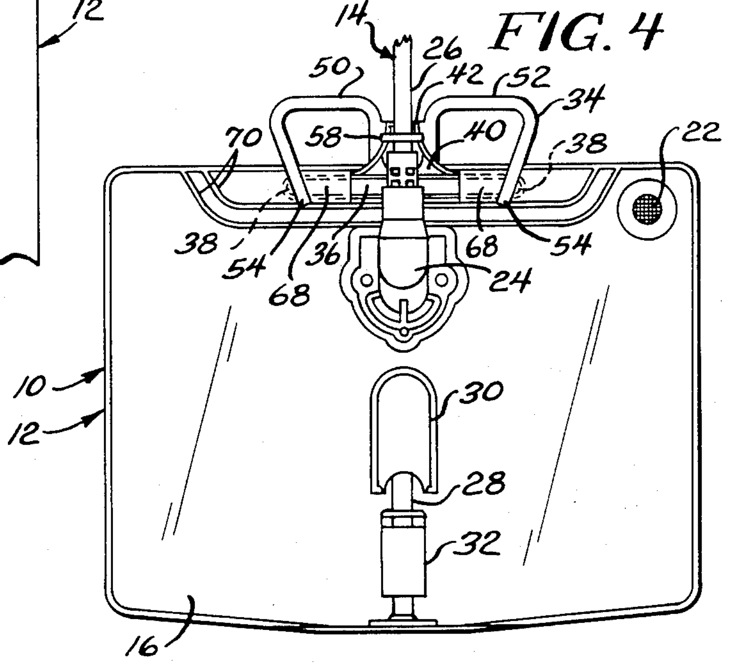

LIQUID DRAINAGE SYSTEM WITH FORMED HINGED SUPPORT SHEET

BACKGROUND OF THE INVENTION

The present invention relates to liquid drainage systems, and more particularly to urine drainage systems.

In the past, urine drainage systems have been known. Such systems may comprise a catheter which is passed through the urethra of a patient until a distal end of the catheter is located in the patient's bladder, a drainage tube connected to a proximal end of the catheter outside the patient's body, and a receptacle having a chamber with a downstream end of the drainage tube communicating with the chamber. In use, urine drains through the catheter and drainage tube into the chamber for retention therein.

Although such systems have operated satisfactorily in the past, the systems are disposable such that they are discarded after a single use. Hence, it is desirable to simplify construction of the systems, and thus reduce their cost to the patient.

SUMMARY OF THE INVENTION

A principal feature of the present invention is the provision of an improved liquid drainage system of simplified construction.

The liquid drainage system of the present invention comprises, a receptacle having a chamber to receive the liquid, and a drainage tube communicating with the chamber. The system has a formed sheet of flexible material, with the sheet being of one-piece construction. The sheet has an elongated bar received in an upper portion of the receptacle, a first connecting portion extending from one side of the bar at a generally central location thereof, a first hinge extending across the sheet at an outer end of the first connecting portion, and a second elongated connecting portion extending from the first hinge on a side of the first hinge opposite the first connecting portion. The second connecting portion is flexed about the first hinge to align the first and second connecting portions in a facing relationship. The sheet has second and third hinges extending along opposed sides of the second connecting portion, and first and second hook members connected to the second and third hinges, with the hook members having downwardly extending outer ends.

A feature of the present invention is that the hook members are movable to a first position generally perpendicular to the receptacle to support the receptacle from an object.

Another feature of the invention is that the hook members are movable to a second position generally aligned with the receptacle with the outer ends of the hook members being located in front of the bar to form a handle to carry the receptacle.

Yet another feature of the invention is that the first connecting portion has a ring joined to the first connecting portion by a hinge, with the drainage tube being received in the ring.

Still another feature of the invention is that the sheet is of simplified construction in order to provide the system at a reduced cost to the patient.

Further features will become more fully apparent in the following description of the embodiments of this invention and from the appended claims.

DESCRIPTION OF THE DRAWINGS

In the drawings:

FIG. 1 is a plan view of a formed sheet for a liquid drainage system of the present invention;

FIG. 2 is a plan view illustrating the sheet as flexed about a first hinge;

FIG. 3 is a fragmentary perspective view illustrating the sheet as secured to an upper portion of the receptacle, and hook members of the sheet in position for supporting the receptacle on an object; and FIG. 4 is a fragmentary plan view of the system illustrating the hook members as positioned to form a handle to carry the receptacle.

DESCRIPTION OF THE PREFERRED EMBODIMENTS

Referring now to FIGS. 3 and 4, there is shown a liquid drainage system generally designated 10 comprising a receptacle 12 and a drainage tube 14. The receptacle 12 has a front wall 16 of flexible plastic material, and a back wall 18 of flexible plastic material, with the front and back walls 16 and 18 being joined at their periphery in order to define a chamber 20 between the front and back walls 16 and 18. With reference to FIG. 4, the receptacle 12 may have a vent 22 with a bacteria filter of known type in order to filter bacteria from the air passing from the atmosphere into the chamber 20. The receptacle 12 has a connector 24 secured to the front wall 16, with the downstream end 26 of the drainage tube 14 being secured to the connector 24, such that the drainage tube 14 communicates with the receptacle chamber 20. The receptacle 12 may have a lower tubular section 28 communicating with a lower portion of the chamber 20, with the outer end of the tubular section 28 being received in a pocket 30 in a storage position of the tubular section 28. When it is desired to empty liquid from the chamber 20, the tubular section 28 is removed from the pocket 30 and a clamp 32 of known type is opened to permit passage of the liquid through the tubular section 28. When drainage of the chamber 20 has been completed, the clamp 32 is closed, and the outer end of the tubular section 28 is inserted into the pocket 30 in order to place the tubular section 28 in the storage position.

In use of the system 10, a catheter (not shown) is passed through the urethra of a patient until a distal end of the catheter is located in the patient's bladder. A proximal end of the catheter located outside the patient's body is connected to an upstream end of the drainage tube 14, and urine drains through the catheter and drainage tube 14 into the chamber 20 for collection therein.

In accordance with the present invention, with reference to FIG. 1, the system 10 has a formed sheet 34 of flexible material, such as a suitable plastic material, e.g., polyethylene, with the sheet 34 being of one-piece construction. The sheet 34 has an elongated bar 36 with opposed outer ends 38. The sheet 34 has a first connecting portion 40 extending from one side of the bar 36 at a generally central location of the bar 36. The sheet 34 has a first hinge 42 of reduced thickness extending across the sheet 34 at an outer end of the first connecting portion 40.

The sheet 34 has a second elongated connecting portion 44 extending from the first hinge 42 on a side of the first hinge 42 opposite the first connecting portion 40. The sheet 34 has second and third hinges 46 and 48 of reduced thickness, respectively, extending along opposed sides of the second connecting portion 44. The sheet 34 also has first and second hook members 50 and 52 connected to the second and third hinges 46 and 48, respectively, with the hook members 50 and 52 having downwardly extending outer ends 54 when the sheet 34 is folded for assembly with the receptacle 12.

As shown, the first connecting portion 40 has a cut-out 56 defining a ring 58. The first connecting portion 40 has a fourth hinge 60 of reduced thickness intermediate the bar 36 and first hinge 42 connecting the ring 58 to the first connecting portion 40. The second connecting portion 44 has a pin 62 adjacent an outer end thereof, and the bar 36 has a flange 64 on the other side of the bar 36 adjacent a central portion thereof, with the flange 64 having an aperture 66 to receive the pin 62.

With reference to FIG. 4, the receptacle 12 has a pair of opposed pockets 68 in an upper portion of the receptacle 12, with the pockets 68 being separated from the chamber 20 by one or more seal lines 70. During assembly of the system 10, the opposed ends 38 of the bar 36 are received in the pockets 68, with the bar 36 serving to stabilize and support the receptacle 12. During further assembly of the system 10, with reference to FIG. 2, the sheet 34 is folded about the first hinge 42 to place the first connecting portion 40 in a facing relationship with the second connecting portion 44. In this configuration, the pin 62 is received in the aperture 66, and the first and second connecting portions 40 and 44 may be secured together by heating and flattening an outer end of the pin 62, with the pin 62 serving to hold the parts together.

With reference to FIGS. 3 and 4, the ring 58 is flexed outwardly from the first connecting portion 40 about the fourth hinge 60, and the drainage tube 14 is received in the ring 58, with the ring 58 stabilizing the drainage tube 14 in an upright position relative to the receptacle 12. With reference to FIG. 3, the hook members 50 and 52 may be flexed about the second and third hinges 46 and 48, respectively, until the hook members 50 and 52 are at a position generally perpendicular to the receptacle 12. In this configuration, the hook members 50 and 52 may be placed on an object, such as a bed rail, in order to support the receptacle 12 from the object. Alternatively, with reference to FIG. 4, the hook members 50 and 52 may be flexed about the second and third hinges 46 and 48, respectively, to a position generally aligned with the receptacle 12, and the outer ends 54 of the hook members 50 and 52 may be placed in front of the bar 36, such that the hook members 50 and 52 form a handle to carry the receptacle 12.

Thus, in accordance with the present invention, the system 10 has a sheet 34 which forms a stabilizer bar 36, a ring 58 to stabilize the drainage tube 14, and hook members 50 and 52 to support the receptacle 12. The sheet 34 is of simplified construction in order to simplify the manufacture and reduce the cost of the system 10 to the patient.

The foregoing detailed description is given for clearness of understanding only, and no unnecessary limitations should be understood therefrom, as modifications will be obvious to those skilled in the art.

We claim:

1. A liquid drainage system, comprising:

a receptacle having a chamber to receive the liquid;

a drainage tube communicating with the chamber;

a formed sheet of flexible material, with said sheet being of one-piece construction, said sheet having an elongated bar received in an upper portion of the receptacle, a first connecting portion extending from one side of the bar at a generally central location thereof, a first hinge extending across the sheet at an outer end of the first connecting portion, a second elongated connecting portion extending from the first hinge on a side of the first hinge opposite the first connecting portion, said second connecting portion being flexed about the first hinge to align the first and second connecting portions in a facing relationship, second and third hinges extending along opposed sides of the second connecting portion, and first and second hook members connected to said second and third hinges, with the hook members having downwardly extending outer ends, said hook members being movable between a first position generally perpendicular to the receptacle to support the receptacle from an object, and a second position generally aligned with the receptacle with the outer ends of the hook members being located in front of said bar to form a handle to carry the receptacle including means for securing the first and second connecting portions in the facing relationship.

2. The system of claim 1 wherein the securing means comprises a first securing member on an outer end of the second connecting portion, and a second securing member adjacent the other side of the bar adjacent a central portion thereof.

3. The system of claim 2 wherein said first and second securing members comprise an interlocking pin and aperture.

4. A liquid drainage system, comprising:

a receptacle having a chamber to receive the liquid;

a drainage tube communicating with the chamber;

a formed sheet of flexible material, with said sheet being of one-piece construction, said sheet having an elongated bar received in an upper portion of the receptacle, a first connection portion extending from one side of the bar at a generally central location thereof, a first hinge extending across the sheet at an outer end of the first connecting portion, a second elongated connecting portion extending from the first hinge on a side of the first hinge opposite the first connecting portion, said second connecting portion being flexed about the first hinge to align the first and second connecting portions in a facing relationship, second and third hinges extending along opposed sides of the second connecting portion, and first and second hook members connected to said second and third hinges, with the hook members having downwardly extending outer ends, said hook members being movable between a first position generally perpendicular to the receptacle to support the receptacle from an object, and a second position generally aligned with the receptacle with the outer ends of the hook members being located in front of said bar to form a handle to carry the receptacle wherein said first connecting portion has a cut-out defining a ring, said first connecting portion having a fourth hinge intermediate the bar and first hinge connecting the ring to the first connecting portion, said ring being flexed outwardly from the first connecting portion with said drainage tube being received in the ring.

* * * * *